(12) United States Patent
Stanczak et al.

(10) Patent No.: US 9,408,550 B2
(45) Date of Patent: Aug. 9, 2016

(54) EVOLVING SERIAL COMPARISON SYSTEM WITH CRITICAL ALERT NOTIFICATIONS

(71) Applicant: Epiphany Cardiography Products, LLC, Midlothian, VA (US)

(72) Inventors: James Stanczak, Arlington Heights, IL (US); Russell Deremer, Midlothian, VA (US); Alan Risse, Camarillo, CA (US)

(73) Assignee: Epiphany Cardiography Products, LLC, Midlothian, VA (US)

( * ) Notice: Subject to any disclaimer, the term of this patent is extended or adjusted under 35 U.S.C. 154(b) by 73 days.

(21) Appl. No.: 14/539,864

(22) Filed: Nov. 12, 2014

(65) Prior Publication Data

US 2015/0133805 A1    May 14, 2015

Related U.S. Application Data (60) Provisional application No. 61/903,706, filed on Nov. 13, 2013.

(51) Int. Cl.

| A61B 5/044 | (2006.01) |
|---|---|
| A61B 5/0452 | (2006.01) |
| A61B 5/0464 | (2006.01) |
| A61B 5/04 | (2006.01) |
| A61B 5/00 | (2006.01) |
| A61B 5/0432 | (2006.01) |
| G06F 19/00 | (2011.01) |

(52) U.S. Cl.
CPC ............. *A61B 5/04525* (2013.01); *A61B 5/044* (2013.01); *A61B 5/04012* (2013.01); *A61B 5/0432* (2013.01); *A61B 5/0464* (2013.01); *A61B 5/746* (2013.01); *A61B 5/7475* (2013.01); *G06F 19/345* (2013.01); *G06F 19/3487* (2013.01)

(58) Field of Classification Search
CPC ............. A61B 5/0452; A61B 5/04012; A61B 5/0464; A61B 5/0402; A61B 5/04525; A61B 5/046; G06F 19/345; G06F 19/3487; G06F 19/34; G06F 19/3431
See application file for complete search history.

(56) References Cited

U.S. PATENT DOCUMENTS

2006/0161066 A1 *   7/2006   Elion .................... A61B 5/044
                                                                600/509

\* cited by examiner

*Primary Examiner* — George Evanisko
(74) *Attorney, Agent, or Firm* — Richards Patent Law P.C.

(57) ABSTRACT

A system for serial comparison of physiological data, including: a controller; a user interface; and a memory including instructions that, when executed by the controller, perform the steps of: receiving from a first data source a current clinical report including first set of physiological data of a patient and computer-generated first interpretive statements; accessing, from the patient file in a patient database, a previous clinical report including a second set of physiological data of the patient and physician-edited interpretive statements; mapping the physician-edited interpretive statements into one or more codes of a structured data format, wherein each code uniquely identifies a medical state; performing a serial comparison between the current clinical report and the previous clinical report to generate serial comparison interpretive statements; providing to a user, via the user interface, the serial comparison interpretive statements; and receiving, via the user interface, current physician-edited interpretive statements.

10 Claims, 5 Drawing Sheets

Interpretation — 61

[Undo] [Clear] [Confirm and Next]

65 → Regular wide complex Tachycardia, origin unclear, cannot exclude V-tach.
Also consider paroxysmal superventricular tachycardia, Atrial flutter with 2/1 block
Tachycardia, ? origin, rate 140
Left bundle branch block pattern
Nonspecific ST-T wave changes
Compared to ECG 08/10/2007 07:27:41
Wide-QRS tachycardia now present
ST (T wave) deviation now present
Sinus rhythm no longer present

Interpretation — 61

[Undo] [Clear] [Confirm and Next]

68 → Normal sinus rhythm, rate 82
Left bundle branch block
Low amplitude P waves.
Compared to ECG 08/11/2007 10:52:03
Wide-QRS tachycardia now present
ST (T wave) deviation now present

60

82 → Electronically Signed On 08-17-11 17:43:09 EDT by Doctor Smith, MD

FIG. 4C

60 → Normal sinus rhythm, rate 82
Left bundle branch block
68 → Low amplitude P waves.
Compared to ECG 08/11/2007 10:52:03
Wide-QRS tachycardia now present
60 → ST (T wave) deviation now present 82 → Electronically Signed On 08-17-11 17:43:09 EDT by Doctor Smith, MD

| | |
|---|---|
| Normal sinus rhythm | 1.0.1 (normal sinus rhythm) |
| "Left bundle branch block" | 7.1.2 intermittent left bundle branch block |
| "Wide-QRS tachycardia" | 8.2.2 wide QRS complex |
| 60 → "ST (T-wave) deviation" | 5.8 Minor ST-T abnormalities — 84 |

EVOLVING SERIAL COMPARISON SYSTEM WITH CRITICAL ALERT NOTIFICATIONS

CROSS-REFERENCE TO RELATED APPLICATIONS

This application incorporates by reference and claims the benefit of priority to U.S. Provisional Patent Application No. 61/903,706 filed Nov. 13, 2013.

BACKGROUND OF THE INVENTION

The present subject matter relates generally to an evolving serial comparison system with critical alert notifications. More specifically, the present invention relates to a serial comparison system where the user may input free-form natural language text corrections that are recognized by the serial comparison system to generate diagnostic codes of a structured data format.

An electrocardiogram (ECG) is noninvasive procedure used to measure the rate and regularity of heartbeats by measuring the electrical activity of the heart over a period of time using electrodes attached to the surface of the skin.

ECGs are the most efficient and effective tool for diagnosing cardiac arrhythmia, myocardial ischemia/infarct (heart attack), among other conditions, and are also useful for measuring the size and position of the heart chambers, the presence of any damage to the heart, and the effects of drugs or devices used to regulate the heart, such as a pacemaker.

An ECG produces a pattern reflecting the electrical activity of the heart and usually requires a trained clinician to interpret it. ECG waveforms often present biological variations, and, thus, the diagnostic value of a single ECG is limited. Comparing a current ECG to previous ECGs of a patient may reduce the limitations of a single ECG. This process is known as visual serial comparison. By examining ECG serial changes over time using visual serial comparison, physicians may make more accurate diagnosis.

Increasingly, computer interpretations of ECG readings are being provided to improve the speed of analysis and action. Commercial systems are available that provide valuable assistance in automated serial ECG comparison analysis. However, about 25-30% of these computer ECG interpretations are wrong. Incorrect ECG interpretations may cause serious medical problems to be overlooked, and may cause further errors in future automated ECG interpretations based on the erroneous ECG interpretation. Thus, review of automated ECG comparisons by physicians remains an important part of the diagnostic process.

Previous systems for the review of automated ECG interpretations required the correction of ECG interpretations using controlled data entry of codes and exact phrases prescribed by the serial comparison algorithms. By requiring entry of codes and exact phrases, previous review systems placed a burden on cardiologists to learn proprietary codes and phrases, or required the additional review step of having a technician to read a written correction of an ECG interpretation and translate the correction into the codes or phrases.

Additionally, automated review and confirmation of ECG readings is often performed not by the treating physician at the place and time of ECG recording but by a reading cardiologists or other trained professionals at later times. Accordingly, if a critical result is found it is important that the result be communicated to the patient's treating physician in a timely manner. Increasingly, providing critical results must be performed in a prescribed manner and logged to meet the standard of care. Accordingly, there is a need for automated reporting and logging of critical results.

Accordingly, there is a need for systems and methods for fast, efficient, easy-to-use review of automated ECG serial comparison interpretations including proper handling of critical alerts, as described herein.

BRIEF SUMMARY OF THE INVENTION

To meet the needs described above and others, the present disclosure provides an evolving serial comparison system with critical alert notifications. A physician user of the serial comparison system may view clinical reports of patient ECG recordings including, e.g., waveforms and automatic interpretations, review and update the automatic interpretations, input diagnostic codes, trigger critical alerts, etc. When updating an automatic interpretation, the user may enter the updates in a free form text box using written English phrases and abbreviations comfortable to the user. The serial comparison system may translate the written English phrases and abbreviations into a structured data format of diagnostic codes, which may then be utilized in future serial comparisons.

The evolving serial comparison system may be provided as a server that users may access over a network. Users may communicate with the serial comparison system using a user interface. The user interface may be a web interface, a native application running on a user machine, a mobile application running on a mobile device, a dedicated device, or any other interface as will be appreciated by those of skill in the art from the examples provided herein.

The serial comparison system may be incorporated into the workflow or environment of a medical practice or hospital. Accordingly, the serial comparison system may interface with various physiological recording and testing devices to receive patient data, access remote servers, such as hospital health information systems storing patient data, and communicate with user devices.

Although described herein as working with electrocardiogram recordings, it is contemplated that the serial comparison system may operate on other physiological data, such as data collected from stress tests, Holter monitoring, defibrillators, pulmonary function testing, event monitoring, pacemaker, mobile telemetry, vital signs, EEG, blood pressure data, sleep monitoring, etc.

Serial comparison begins when a medical device, such as a cardiograph, generates a clinical report that may include physiological data and test results, e.g., cardiogram waveform and measurements. The clinical report may include interpretive statements from an algorithm run on the waveform and measurements by the medical device. In an embodiment, interpretive statements are a diagnostic classification of the state and behavior of the heart as determined from a cardiogram waveform. The serial comparison system may receive the clinical report via a direction connection, WiFi, LAN, the Internet or other network, via the network interface.

Upon receiving the clinical report, the social comparison system may access a patient file and retrieve a previous clinical report for the patient. The previous clinical report may include a previous waveform and a previous physician edited interpretive statements. The serial comparison system may include a patient data database to access the patient file. Alternatively, the serial comparison system may communicate with a hospital patient records management system to access the patient file. The serial comparison system may store the new clinical report in the patient file.

The previous physician edited interpretive statements may be the stored edits of the user to previously computer-generated serial comparison interpretive statements. If the previous clinical report is available, the serial comparison system maps the previous physician edited interpretive statements into one or more diagnostic codes of a structured data format to put the previous physician edited interpretive statements into a format usable with a serial comparison algorithm. Each code may uniquely identify a medical state. If no previous clinical report is found, the serial comparison system inserts the statement, "no previous report is available for comparison," into the interpretive statements.

Using the diagnostic codes, the serial comparison system may perform an automated serial comparison of the previous clinical report and the new clinical report to generate new serial comparison interpretive statements. The automated serial comparison may begin by determining the diagnostic codes of the interpretive statements from both the previous clinical report and the new clinical report. The cardiogram waveform and measurements may be examined in those diagnostic codes to determine whether waveform changes have occurred in those categories. If no significant waveform changes are detected in based on the diagnostic code, the serial comparison system may add a modifier "remains" to an interpretive statement add it to the serial comparison interpretive statements to the interpretive statement. If significant waveform changes are detected, a "more prominent" or "less prominent" modifier may be added.

If the new clinical report includes an interpretive statement associated with a diagnostic code not present in the previous clinical report, a modifier "now present" may be added to the interpretive statement added to the serial comparison interpretive statements. If the previous clinical report includes an interpretive statement and there is no interpretive statement in that category in the new clinical report, the modifier "now absent" is added to the interpretive statement, otherwise the clinical report keeps the interpretive statement with the modifier "remains." Additionally, interpretive statements may be added to the serial comparison interpretive statements take into account rhythm changes, secondary rhythm changes, heart rate changes, etc.

Next, the serial comparison system may display a serial comparison screen via the user interface to display the clinical report to users. The serial comparison screen permits the user to view the clinical report and the previous clinical report side-by-side. Users may include a physician assisting in editing the clinical report. As shown, the serial comparison screen may include the previous waveform and previous physician edited interpretive statements of the previous clinical report. From the present clinical report is displayed the waveform and the freshly generated serial comparison interpretive statements. The serial comparison interpretive statements are displayed in the user-editable interpretation box. A user may correct the serial comparison interpretive statements in the interpretations box and the resulting physician edited interpretive statements may be stored in the patient file.

A search box may be provided to permit the user to search for interpretive statements. When the search box is active, as each character of a search string is entered, the serial comparison system may limit the interpretive statements in the library box to those interpretive statements matching the search string as entered at that point in time. This may permit the user to select the correct interpretive statements from the results list without having to input a full matching search string. Likewise, a categories dialog box may be provided to permit the user to limit the results list to particular categories of interpretive statements physician edited interpretive statements.

As noted, the user may input free-form text input into the interpretation box, or edit the text of the serial comparison interpretive statements already present to generate physician edited interpretive statements. In some embodiments, the user may be permitted to input free-form text using speech recognition. In other embodiments, the user may be permitted to input free-form text using handwriting recognition. After editing, the user may confirm the updates to the clinical report by clicking a save changes button. The user may create an electronic signature to sign the physician edited interpretive statements.

In some embodiments, the step of mapping the physician-edited interpretive statements to one or more diagnostic codes of a structured data format may be carried out by mapping sub-steps. In the first step, the physician edited interpretive statements may be parsed to extract individual interpretive statements. Parsing may require the serial comparison system to first normalize the physician edited interpretive statements into a normalized text form. For example, the serial comparison system may convert audio recordings of verbal physician edited interpretive statements to text. Similarly, the serial comparison system may convert handwriting to text. After physician edited interpretive statements have been normalized to text, spelling correction, grammatical correction and normalization, removal of punctuation, etc., may then normalize the resulting textual corrections. Interpretive statements may then be parsed by splitting the physician edited interpretive statements into two or more sub-strings.

In the next step, the serial comparison system classifies at least one substring to correspond to at least one code of a structured data format. Classification may be accomplished by performing a lookup of the interpretive statement in the interpretive statements database. The interpretive statements database may include known interpretive statements including spelling, abbreviations and acronym variations of the known interpretive statements. For each known interpretative statement extracted, the serial comparison system may lookup the diagnostic code associated with the interpretative statement and store the diagnostic code in the clinical report or use it to perform serial comparison to generate serial comparison interpretive statements. If stored, the updated clinical report may then be stored in a patient data database for treatment, future use in serial comparison analysis, to trigger critical alerts, generate reports, etc. The steps of parsing and classifying may be iterated in order to fully parse the physician edited interpretive statements. For example, at the parsing step, a candidate interpretive statement from a substring of the physician edited interpretive statements may be generated and checked in the classifying step. This process may be repeated until all interpretive statements are identified or until all combinations of substrings are checked.

After a user has saved changes to the clinical report, the serial comparison system may check the physician edited interpretive statements for one or more interpretative statements that require a critical alert to be issued. If one or more of the physician edited interpretive statements requires a critical alert, the serial comparison system may remind the physician to issue a critical alert. A popup critical alert box including physician edited interpretive statements may be displayed above the serial comparison screen to remind the physician to issue a critical alert. The popup critical alert box may identify the interpretative statement requiring a critical alert. The user may select an issue critical alert button to trigger the issuance of a critical alert. Alternatively, the user may cancel the popup critical alert box to resume normal use by selecting the cancel button. After editing, the user may confirm the updates to the clinical report by clicking a save changes button. In an embodiment, the criteria for triggering a reminder to issue a critical alert may be an interpretation indicating acute myocardial infarction; tachycardia>one hundred sixty beats per minute; Mobitz II heart block; pacemaker failure; ventricular tachycardia; bradycardia<forty beats per minute; and a new onset of a left bundle branch block.

Similarly, a send alert button may be provided to permit the user to manually issue a critical alert. If a critical alert is issued, the serial comparison system may then log the critical alert. Next, the critical alert may be logged in the patient data database of the serial comparison system or an associated hospital patient records management system.

The serial comparison system may maintain a log of all physician input in the physician-edited interpretive statements that are unrecognized by the serial comparison system. The log may be securely transferred, via secure protocol, to the manufacturer for review. For example, the log may be transferred to a terms server controlled by the manufacturer. Clinically important but previously unrecognized interpretive statements in the log may then be added to a remote updates that may be regularly pushed out by the terms server at step to serial comparison systems running at various medical institutions allowing the serial comparison systems to evolve for the user over time.

In an embodiment, the interpretive statements database may be periodically updated by a remote update from a terms server. The terms server may in turn execute an update method to update the interpretive statements database of remote serial comparison system, the method comprising the steps of: receiving, from one or more serial comparison system, a log of logged interpretive statements that failed to match any interpretive statements in the interpretive statements database; providing the logged data to a user via a user interface; receiving, from the user, a mapping of the logged interpretive statements of the log to one or more diagnostic codes of the structured data format; and transmitting, to the serial comparison systems, the mapping of the logged interpretive statements to one or more diagnostic codes of the structured data format.

The serial comparison system may be a computer including instructions stored in a memory that, when executed by a controller, carry out the functionality disclosed herein. Further the serial comparison system may be a computer in communication with user devices, such as user computers, tablets, and mobile devices to provide the functionality disclosed herein. Even further, in some embodiments, the serial comparison system may be a subcomponent of a data records management or practice management system and may be in communication with other subcomponents or process to carry out the functionality described herein.

In an embodiment, a system for serial comparison of physiological data, includes: a controller; a user interface; and a memory including instructions that, when executed by the controller, perform the steps of: receiving from a first data source a current clinical report including first set of physiological data of a patient and computer-generated first interpretive statements; accessing, from the patient file in a patient database, a previous clinical report including a second set of physiological data of the patient and physician-edited interpretive statements; mapping the physician-edited interpretive statements into one or more codes of a structured data format, wherein each code uniquely identifies a medical state; performing a serial comparison between the current clinical report and the previous clinical report to generate serial comparison interpretive statements; providing to a user, via the user interface, the serial comparison interpretive statements; and receiving, via the user interface, current physician-edited interpretive statements.

In some embodiments, the system further includes a mapping dictionary database including a lookup table of interpretive statements, wherein each interpretive statement maps to at least one of the codes of the structured data format. Also, in some embodiments, the system further includes a network interface, and wherein the memory further includes instructions that, when executed by the controller, perform the step of: storing the current physician-edited interpretive statements as a part of the current clinical report in the patient file in the patient database.

In some embodiments, the system further includes a network interface, and wherein the memory further includes instructions that, when executed by the controller, perform the step of: receiving, from a remote server via the network interface, an update to the mapping dictionary database. Additionally, in some embodiments, the system further includes a network interface, and wherein the memory further includes instructions that, when executed by the controller, perform the steps of: detecting an unknown interpretative statement in the physician notes; and transmitting the unknown interpretative statement to a remote server.

In some embodiments, the physiological data is electrocardiographic data. And, in some embodiments, the step of translating the free form text input from a second data source into one or more codes of a structured data format, includes the sub-steps of: parsing the free form text input into two or more substrings; and classifying at least one substring to correspond to at least one code of a structured data format. Further, in some embodiments, the first representation is a machine-generated serial comparison.

In some embodiments, the memory further includes instructions that, when executed by the controller, perform the step of: if one of the one or more codes of a structured data format meets a criteria for issuing a critical alert, providing to a user, via the user interface, a prompt to issue a critical alert. Moreover, in some embodiments, the criteria for issuing a critical alert is a code indicating one of acute myocardial infarction; tachycardia of greater than one hundred sixty beats per minute, a Mobitz II heart block; pacemaker failure; ventricular tachycardia; bradycardia of less than 40 beats per minute; and a new onset of a left bundle branch block.

Finally, in some embodiments, the memory further includes instructions that, when executed by the controller, perform the step of: receiving, via the user interface, a user input in response to the prompt to issue a critical alert; if the user input indicates that a critical alert is to be issued, logging the critical alert in the patient file in the patient database.

By providing mechanisms to quickly review ECG interpretation and trigger critical alerts, the serial comparison system provides for fast, efficient review of automated ECG interpretations. While the present disclosure is disclosed in the context of ECG interpretations, it is contemplated that the mechanisms described may be applied to automated review and reporting of many kinds of physiological data and testing.

An object of the invention is to ease the burden on cardiologists to learn proprietary codes and phrases to use serial comparison editing software.

Another object of the invention is to reduce failures to issue critical alerts and to improve critical alert management.

An advantage of the invention is that it provides users an intuitive way to input corrections to interpretive statements using natural language.

Another advantage of the invention is that it provides appropriate reminders to trigger a critical alert when appropriate.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
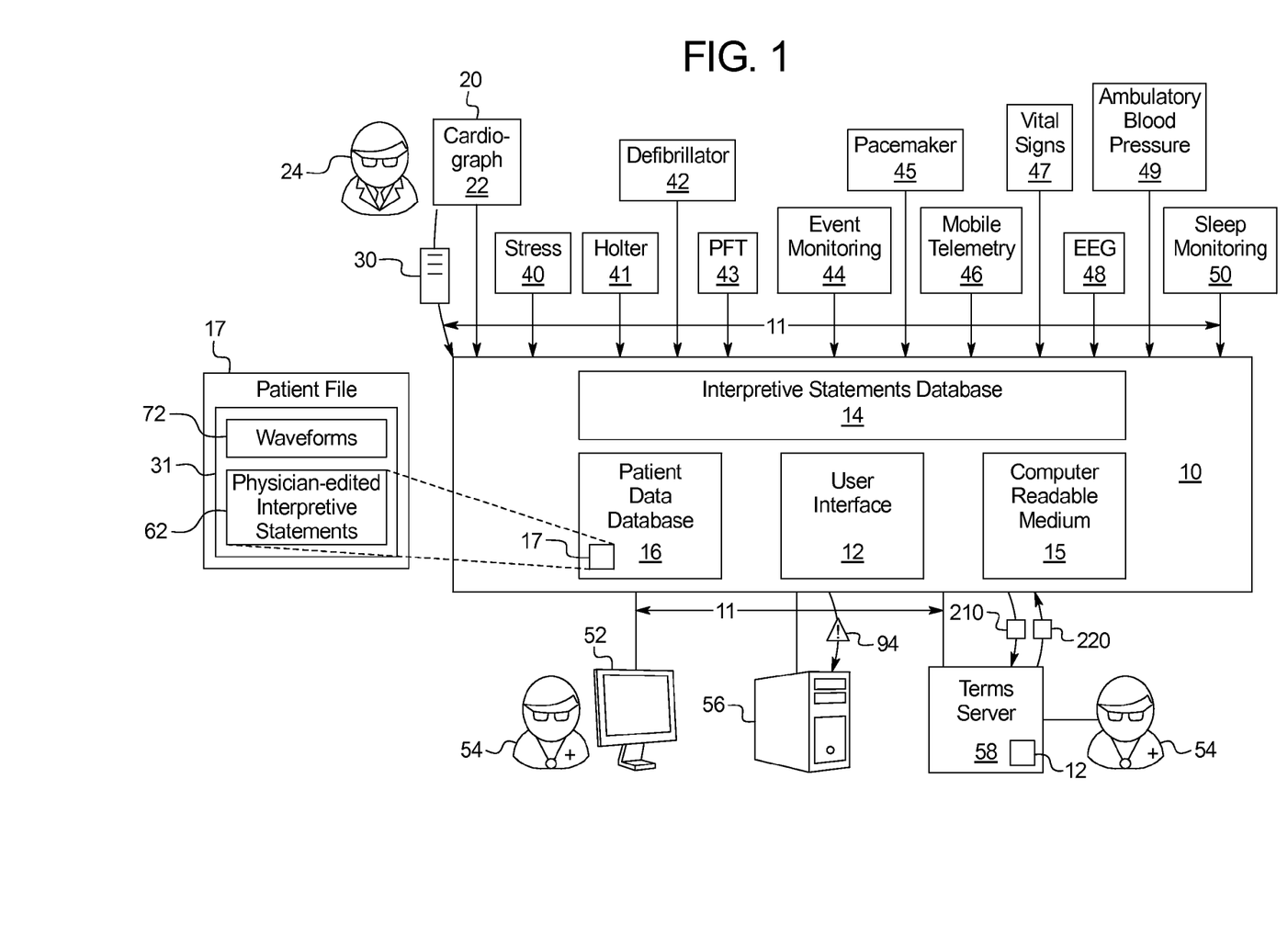
FIG. 1 is a schematic diagram illustrating the ecosystem of an example of the serial comparison system.
Figure 2:
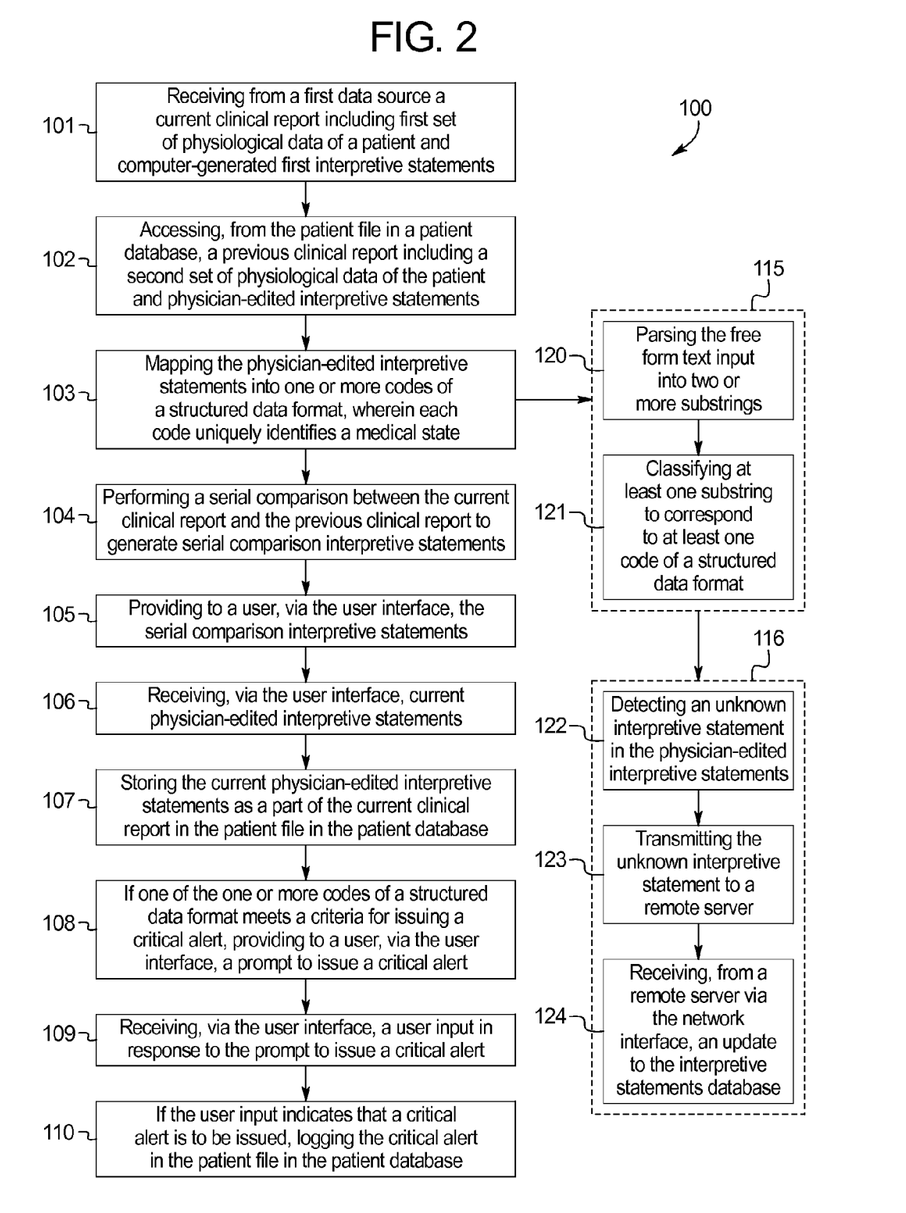
FIG. 2 is a flowchart illustrating the steps the example of the serial comparison system of FIG. 1 performs to perform a serial comparison and trigger critical alerts.

FIG. 1 is a diagram illustrating the ecosystem of the serial comparison system 10. FIG. 2 is a flowchart illustrating the steps the serial comparison system 10 performs to permit a user 54 to view and edit clinical reports 30 of patient ECG recordings and trigger critical alerts 94.

Figure 3:
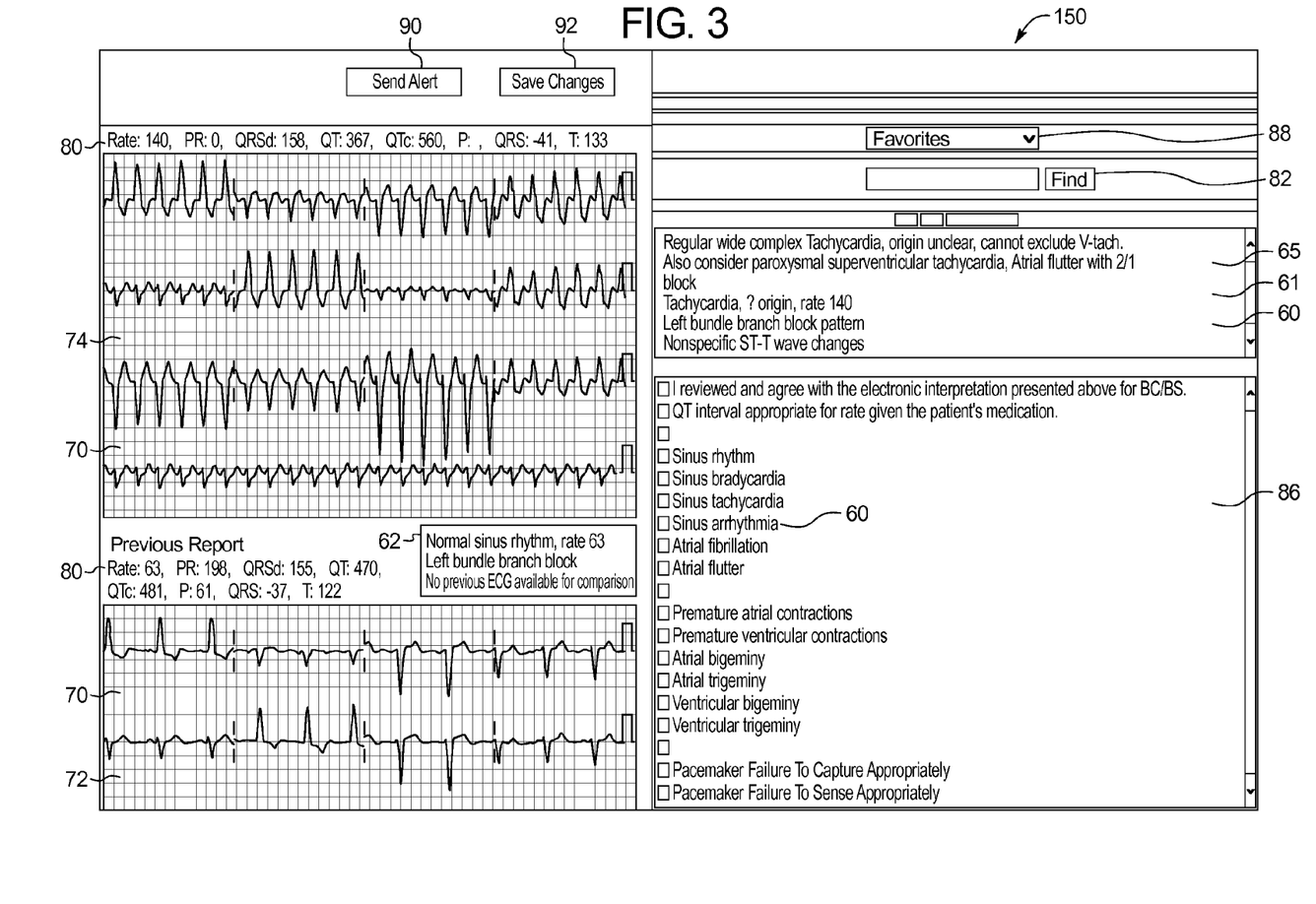
FIG. 3 is an example screenshot that illustrates an example serial interpretation screen of a user interface for serial comparison using the serial comparison system of FIG. 1.

Serial comparison begins at step 101 when a medical device 20, such as a cardiograph 22, generates a clinical report 30 that may include physiological data and test results, e.g., cardiogram waveform 70 and measurements 80 (FIG. 3). The clinical report 30 may include interpretive statements 60 from an algorithm run on the waveform 70 and measurements 80 by the medical device 20. In an embodiment, interpretive statements 60 are a diagnostic classification of the state and behavior of the heart as determined from a cardiogram waveform 70. The serial comparison system 10 may receive the clinical report 30 via a direction connection, WiFi, LAN, the Internet or other network, via the network interface 11.

Upon receiving the clinical report 30, at step 102, the social comparison system 10 may access a patient file 17 and retrieve a previous clinical report 31 for the patient 24. The previous clinical report 31 may include a previous waveform 72 and a previous physician edited interpretive statements 62. The serial comparison system 10 may include a patient data database 16 to access the patient file 17. Alternatively, the serial comparison system 10 may communicate with a hospital patient records management system 56 to access the patient file 17. The serial comparison system 10 may store the new clinical report 30 in the patient file 17.

The previous physician edited interpretive statements 62 may be the stored edits of the user 54 to previously computer-generated serial comparison interpretive statements 56. If the previous clinical report 31 is available, at step 103 and as further shown with respect to FIGS. 4a to 4d, the serial comparison system 10 maps the previous physician edited interpretive statements 62 into one or more diagnostic codes 84 of a structured data format to put the previous physician edited interpretive statements 62 into a format usable with a serial comparison algorithm. Each diagnostic code 84 may uniquely identify a medical state. If no previous clinical report 30 is found, the serial comparison system 10 inserts the statement "No previous report is available for comparison" into the interpretive statements 60 and proceeds to step 105.

Using the diagnostic codes 84, at step 104, the serial comparison system 10 may perform an automated serial comparison of the previous clinical report 31 and the new clinical report 30 to generate new serial comparison interpretive statements 65. The automated serial comparison may begin by determining the diagnostic codes 84 of the interpretive statements 60 from both the previous clinical report 31 and the new clinical report 30. The cardiogram waveform 70 and measurements 80 may be examined in those diagnostic codes 84 to determine whether waveform changes have occurred in those categories. If no significant waveform changes are detected for a diagnostic code 84, the serial comparison system 10 may add a modifier "remains" to an interpretive statement 60 to generate a new serial comparison interpretive statement 65. If significant waveform changes are detected, a "more prominent" or "less prominent" modifier may be added.

If the new clinical report 30 includes an interpretive statement 60 corresponding to a diagnostic code 84 not present in the previous clinical report 31, a modifier "now present" may be added to the interpretive statement 60 added to the serial comparison interpretive statements 65. If the previous clinical report 31 includes an interpretive statement 60 and there is no interpretive statement 60 in that category in the new clinical report 30, the modifier "now absent" is added to the interpretive statement 60, otherwise the clinical report 30 keeps the interpretive statement 60 with the modifier "remains". Additionally, interpretive statements 60 may be added to the serial comparison interpretive statements 65 take into account rhythm changes, secondary rhythm changes, heart rate changes, etc.

Next, at step 105, the serial comparison system 10 displays a serial comparison screen 150 via the user interface 12 to display the clinical report 30 to users 54. The serial comparison screen 150 permits the user 54 to view the clinical report 30 and the previous clinical report 31 side-by-side. Users 54 may include a physician assisting in editing the clinical report 30. As shown, the serial comparison screen 150 may include the previous waveform 72 and previous physician edited interpretive statements 62 of the previous clinical report 30. From the present clinical report 30 is displayed the waveform 70 and the freshly generated serial comparison interpretive statements 65. The serial comparison interpretive statements 65 are displayed in the user-editable interpretation box 61. A user 54 may correct the serial comparison interpretive statements 65 in the interpretations box 61 and the resulting physician edited interpretive statements 68 may be stored in the patient file 17.

A search box 82 may be provided to permit the user 54 to search for interpretive statements 60. When the search box 82 is active, as each character of a search string is entered, the serial comparison system 10 may limit the interpretive statements 60 in the library box to those interpretive statements 60 matching the search string as entered at that point in time. This may permit the user 54 to select the correct interpretive statements 60 from the results list 86 without having to input a full matching search string. Likewise, a categories dialog box 88 may be provided to permit the user 54 to limit the results list 86 to particular categories of interpretive statements 60.

As discussed further below with respect to FIG. 4b, the user 54 may input free-form text input into the interpretation box 61, or edit the text of the serial comparison interpretive statements 65 already present to generate physician edited interpretive statements 68. In some embodiments, the user 54 may be permitted to input free-form text using speech recognition. In other embodiments, the user 54 may be permitted to input free-form text using handwriting recognition. After editing, the user 54 may confirm the updates to the clinical report 30 by clicking a save changes button 92.

Figure 4A:
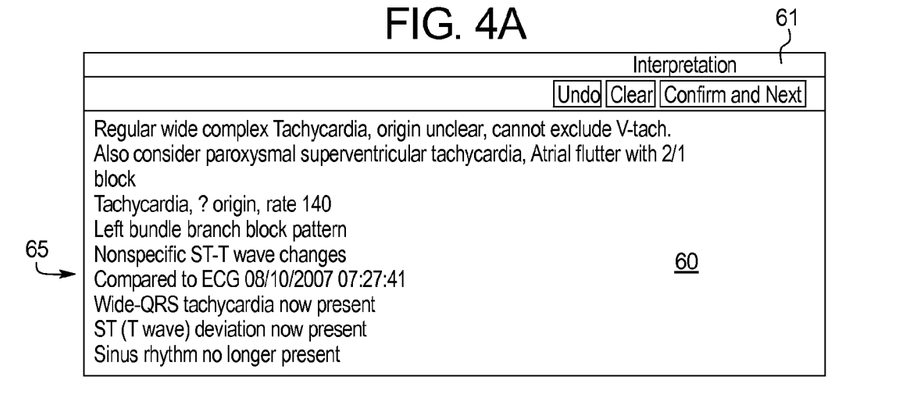
FIG. 4a is an example screenshot that illustrates the interpretation box upon opening a clinical report including computer-generated serial comparison interpretive statements.
Figure 4B:
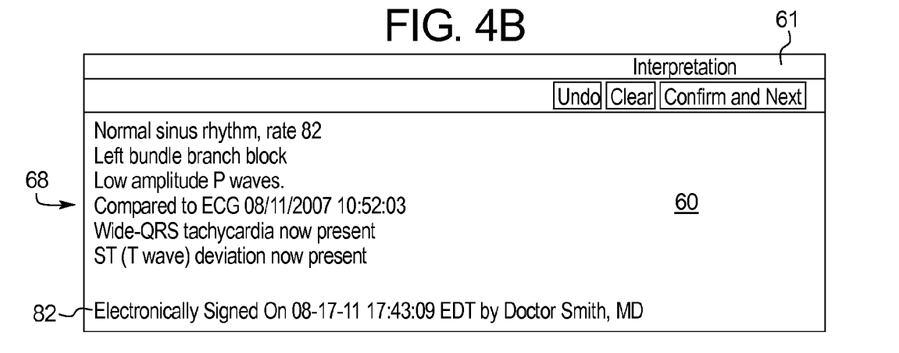
FIG. 4b is an example screenshot that illustrates the interpretation box of the serial comparison screen, displayed via the user interface, after the user has edited the serial comparison interpretive statements to create updated interpretation of the physiological data.

FIGS. 4a-4d illustrate the processing steps of the interpretive statements 60. FIG. 4a illustrates the interpretation box 61 upon opening a clinical report 30. The new serial comparison interpretive statements 65 are pre-populated into the interpretation box 61. The interpretation box 61 may be a free form text input box to permit the user 54 to edit the new serial comparison interpretive statements 65, delete one or more interpretive statements 60 of the new serial comparison interpretive statements 65, and add interpretive statements 60. FIG. 4b illustrates the interpretation box 61 after the user 54 has edited the serial comparison interpretive statements 65 to create an updated interpretation of the physiological data. The user 54 may create an electronic signature 82 to sign the physician edited interpretive statements 68.

Figure 4C:
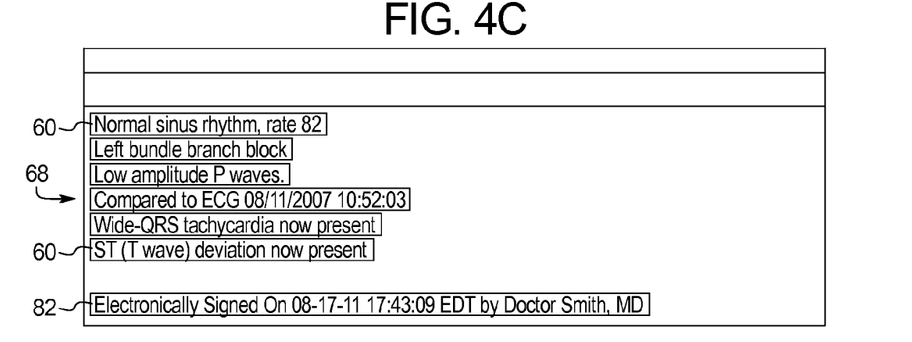
FIG. 4c is an example screenshot that is a stylized diagram illustrating parsing of the physician edited interpretive statements to extract individual interpretive statements.
Figure 4D:
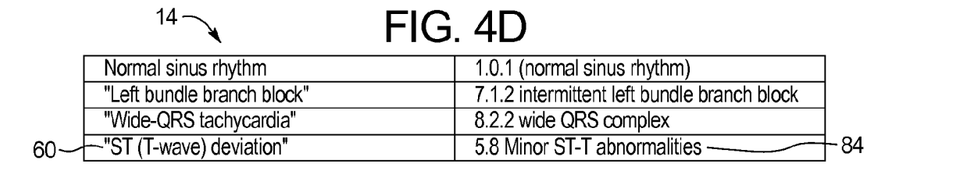
FIG. 4d is an example screenshot that is an example of the logical structure of the interpretive statements database illustrating the relationship between physician edited interpretive statements and diagnostic codes for use during serial comparison.

Returning to step 103, the step of mapping the physician-edited interpretive statements 68 to one or more diagnostic codes 84 of a structured data format may be carried out by the mapping sub-steps 115 as shown in FIGS. 4c and 4d.

As shown in FIG. 4c, at step 120, the physician edited interpretive statements 68 may be parsed to extract individual interpretive statements 60. Parsing may require the serial comparison system 10 to first normalize the physician edited interpretive statements 68 into a normalized text form. For example, the serial comparison system 10 may convert audio recordings of verbal physician edited interpretive statements 68 to text. Similarly, the serial comparison system 10 may convert handwriting to text. After physician edited interpretive statements 68 have been normalized to text, spelling correction, grammatical correction and normalization, removal of punctuation, etc., may then normalize the resulting textual corrections. Interpretive statements 60 may then be parsed by splitting the physician edited interpretive statements 68 into two or more sub-strings.

At step 121, the serial comparison system 10 classifies at least one substring to correspond to at least one diagnostic code 84 of a structured data format. Classification may be accomplished by performing a lookup of the interpretive statement 60 in the interpretive statements database 14. The interpretive statements database 14 may include known interpretive statements 60 including spelling, abbreviations and acronym variations of the known interpretive statements 60. For each known interpretative statement 60 extracted, the serial comparison system 10 may lookup the diagnostic code 84 associated with the interpretative statement 60 and store the diagnostic code 84 in the clinical report 30 or use it to perform serial comparison to generate serial comparison interpretive statements 65. If stored, the updated clinical report 30 may then be stored in a patient data database 16 for treatment, future use in serial comparison analysis, to trigger critical alerts 94, generate reports, etc. The steps of parsing 120 and classifying 121 may be iterated in order to fully parse the physician edited interpretive statements 68. For example, at the parsing step 120, a candidate interpretive statement 60 from a substring of the physician edited interpretive statements 68 may be generated and checked in the classifying step 121. This process may be repeated until all interpretive statements 60 are identified or until all combinations of substrings are checked.

Figure 5:
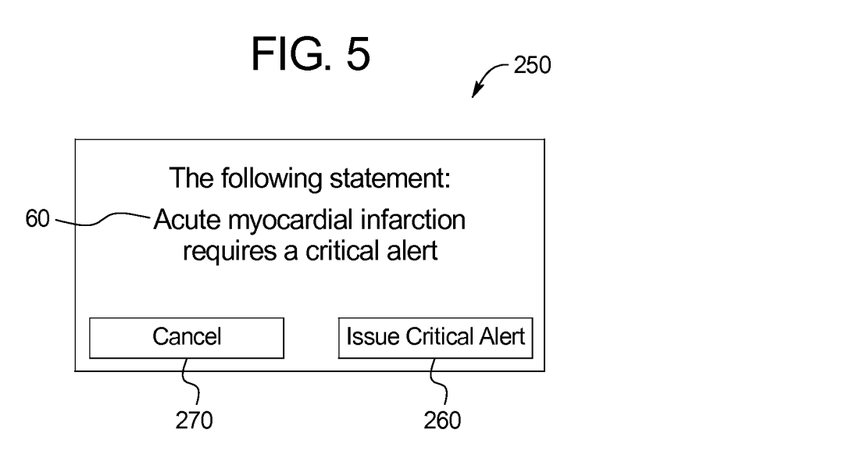
FIG. 5 is an example popup critical alert box that may be displayed by the user interface to remind the physician to issue a critical alert.

After a user 54 has saved changes to the clinical report 30, at step 108, the serial comparison system 10 may check the physician edited interpretive statements 68 for interpretative statement 60 that require a critical alert 94 to be issued. If the physician edited interpretive statements 68 requires a critical alert 94, the serial comparison system 10 may remind the physician to issue a critical alert 94. As shown in FIG. 5, a popup critical alert box 250 including interpretive statements 60 may be displayed above the serial comparison screen 150 to remind the physician to issue a critical alert 94. The popup critical alert box 250 may identify the interpretative statement 60 requiring a critical alert 94. At step 108, the user 54 may select an issue critical alert button 260 to trigger the issuance of a critical alert 94. Alternatively, the user 54 may cancel the popup critical alert box 250 to resume normal use by selecting the cancel button 270. After editing, the user 54 may confirm the updates to the clinical report 30 by clicking a save changes button 92. In an embodiment, the criteria for triggering a reminder to issue a critical alert 94 may be an interpretation indicating acute myocardial infarction; tachycardia>160 beats per minute; Mobitz II heart block; pacemaker failure; ventricular tachycardia; bradycardia<40 beats per minute; and a new onset of a left bundle branch block.

Similarly, a send alert button 90 may be provided to permit the user 54 to manually issue a critical alert 94. If a critical alert 94 is issued, the serial comparison system 10 may then log the critical alert 94. At step 109, the critical alert 94 may be logged in the patient data database 16 of the serial comparison system 10 or an associated hospital patient records management system 56. Alternatively, the rejection of a popup critical alert box 250 or other failure to issue a critical alert 94 may be logged to record that the critical alert 94 was affirmatively not issued.

In an embodiment, a method 100 for serial comparison of physiological data executed by the serial comparison system, as shown in FIG. 2, includes the steps of: step 101 of receiving from a first data source a current clinical report including first set of physiological data of a patient and computer-generated first interpretive statements; step 102 of accessing, from the patient file in a patient database, a previous clinical report including a second set of physiological data of the patient and physician-edited interpretive statements; step 103 of mapping the physician-edited interpretive statements into one or more codes of a structured data format, wherein each code uniquely identifies a medical state; step 104 of performing a serial comparison between the current clinical report and the previous clinical report to generate serial comparison interpretive statements; step 105 of providing to a user, via the user interface, the serial comparison interpretive statements; step 106 of receiving, via the user interface, current physician-edited interpretive statements; step 107 of storing the current physician-edited interpretive statements as a part of the current clinical report in the patient file in the patient database; if one of the one or more codes of a structured data format meets a criteria for issuing a critical alert, at step 108, providing to a user, via the user interface, a prompt to issue a critical alert; step 109 of receiving, via the user interface, a user input in response to the prompt to issue a critical alert; and at step 110, if the user input indicates that a critical alert is to be issued, logging the critical alert in the patient file 17 in the patient database 16.

In an embodiment, mapping sub-steps 116 for updating the interpretive statements database executed by the serial comparison system 10 includes the steps of: step 122 of detecting an unknown interpretative statement in the physician notes; step 123 of transmitting the unknown interpretative statement to a remote server; and step 124 of receiving, from a remote server via the network interface, an update to the interpretive statements database 14.

Step 122 may be accomplished by the serial comparison system 10 maintaining a log 210 of all physician input in the physician-edited interpretive statements 68 that are unrecognized by the serial comparison system 10. The log 210 may be securely transferred, via secure protocol, to the manufacturer for review at step 123, for example, the log 210 may be transferred to a terms server 58 controlled by the manufacturer. Clinically important but previously unrecognized interpretive statements 60 in the log 210 may then be added to a remote updates 220 that may be regularly pushed out by the terms server 58 at step 124 to serial comparison systems 10 running at various medical institutions allowing the serial comparison systems 10 to evolve for the user 54 over time.

Figure 6:
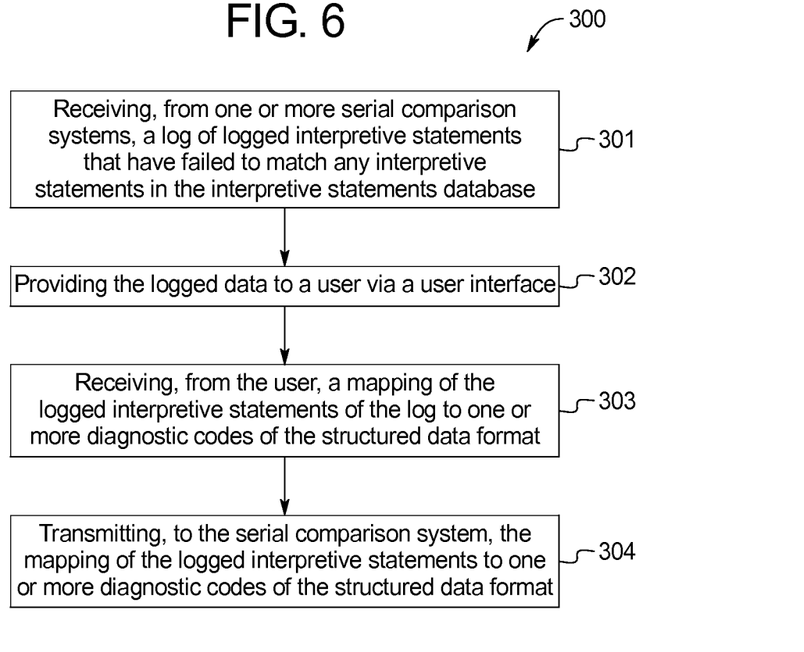
FIG. 6 is a flow chart illustrating an update method performed by a remote terms server to update the interpretive statements database of the serial comparison system of FIG. 1.

In an embodiment, at step 124, the interpretive statements database 14 may be periodically updated by a remote update 22 from a terms server 58. The terms server 58 may in turn execute an update method 300 shown in FIG. 6 to update the interpretive statements database 14 of remote serial comparison systems 10, the method comprising the steps of: step 301 of receiving, from one or more serial comparison system 10, a log 210 of logged interpretive statements 60 that failed to match any interpretive statements 60 in the interpretive statements database 14; step 302 of providing the logged data to a user 54 via a user interface 14; step 303 of receiving, from the user 54, a mapping of the logged interpretive statements 60 of the log 210 to one or more diagnostic codes 84 of the structured data format; and step 304 of transmitting, to the serial comparison systems 10, the mapping of the logged interpretive statements 60 to one or more diagnostic codes 84 of the structured data format.

Returning again to FIG. 1, in some embodiments, the serial comparison system 10 may receive other physiological data in the clinical report 30, such as data collected from stress tests 40, Holter monitoring 41, defibrillators 42, pulmonary function testing 43, event monitoring 44, pacemaker 45, mobile telemetry 46, vital signs 47, EEG 48, blood pressure data 49, sleep monitoring 50, etc. The clinical report 30 may be received from connected monitoring and testing medical devices 20 and may include computer generated interpretive statements 60.

Aspects of the systems and methods described herein are controlled by one or more controllers. The one or more controllers may be adapted run a variety of application programs, access and store data, including accessing and storing data in associated databases, and enable one or more interactions via the user interface. Typically, the one or more controllers are implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a central control processing system utilizing a central processing unit (CPU), memories and an interconnect bus. The CPU may contain a single microprocessor, or it may contain a plurality of microprocessors for configuring the CPU as a multi-processor system. The memories include a main memory, such as a dynamic random access memory (DRAM) and cache, as well as a read only memory, such as a PROM, EPROM, FLASH-EPROM, or the like. The system may also include any form of volatile or non-volatile memory. In operation, the main memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output displays (e.g., monitors, printers, touchscreen, motion-sensing input device, etc.) and one or more input mechanisms (e.g., keyboard, mouse, voice, touch, bioelectric devices, magnetic reader, RFID reader, barcode reader, touchscreen, motion-sensing input device, etc.) serving as one or more user interfaces for the controller. For example, the one or more controllers may include a graphics subsystem to drive the output display. The links of the peripherals to the system may be wired connections or use wireless communications.

Although summarized above as a PC-type implementation, those skilled in the art will recognize that the one or more controllers also encompasses systems such as host computers, servers, workstations, network terminals, and the like. Further one or more controllers may be embodied in a device 10, such as a mobile electronic device, like a smartphone or tablet computer. In fact, the use of the term controller is intended to represent a broad category of components that are well known in the art.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as main memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, any other memory chip or cartridge, or any other medium from which a computer can read programming code and/or data. Many of these forms of computer readable media may be involved in carrying one or more sequences of one or more instructions to a processor for execution.

It should be noted that various changes and modifications to the presently preferred embodiments described herein will be apparent to those skilled in the art. Such changes and modifications may be made without departing from the spirit and scope of the present invention and without diminishing its attendant advantages.

We claim:

1. A system for serial comparison of physiological data, comprising:
   a controller;
   a user interface; and
   a memory including instructions that, when executed by the controller, perform the steps of:
   receiving from a first data source a current clinical report including a first set of physiological data of a patient and computer-generated first interpretive statements;
   accessing, from a patient file in a patient database, a previous clinical report including a second set of physiological data of the patient and physician-edited interpretive statements;
   mapping the physician-edited interpretive statements into one or more codes of a structured data format and updating the previous clinical report with the one or more codes, wherein each code uniquely identifies a medical state;
   performing a serial comparison between the current clinical report and the updated previous clinical report and generating serial comparison interpretive statements from the serial comparison;
   providing to a user, via the user interface, the serial comparison interpretive statements; and
   receiving, via the user interface, current physician-edited interpretive statements.

2. The system of claim 1, wherein the system further includes a mapping dictionary database including a lookup table of interpretive statements, wherein each interpretive statement maps to at least one of the codes of the structured data format.

3. The system of claim 2, wherein the system further includes a network interface, and wherein the memory further includes instructions that, when executed by the controller, perform the step of:
   receiving, from a remote server via the network interface, an update to the mapping dictionary database.

4. The system of claim 1, wherein the system further includes a network interface, and wherein the memory further includes instructions that, when executed by the controller, perform the step of:
   storing the current physician-edited interpretive statements as a part of the current clinical report in the patient file in the patient database.

5. The system of claim 1, wherein the system further includes a network interface, and wherein the memory further includes instructions that, when executed by the controller, perform the steps of:
   detecting an unknown interpretative statement in the physician-edited interpretive statements; and
   transmitting the unknown interpretative statement to a remote server.

6. The system of claim 1, wherein the physiological data is electrocardiographic data.

7. The system of claim 1, wherein the step of mapping the physician-edited interpretive statements into the one or more codes of the structured data format and updating the previous clinical report with the one or more codes, includes the sub-steps of:
   parsing the physician-edited interpretive statements into two or more sub strings; and
   classifying at least one substring to correspond to at least one code of a structured data format.

8. The system of claim 1, wherein the memory further includes instructions that, when executed by the controller, perform the step of:
   when one of the one or more codes of a structured data format meets a criteria for issuing a critical alert, providing to a user, via the user interface, a prompt to issue a critical alert.

9. The system of claim 8, wherein the criteria for issuing a critical alert is a code indicating one of acute myocardial infarction; tachycardia of greater than one hundred sixty beats per minute, a Mobitz II heart block; pacemaker failure; ventricular tachycardia; bradycardia of less than 40 beats per minute; and a new onset of a left bundle branch block.

10. The system of claim 8, wherein the memory further includes instructions that, when executed by the controller, perform the step of:
    receiving, via the user interface, a user input in response to the prompt to issue a critical alert;
    when the user input indicates that a critical alert is to be issued, logging the critical alert in the patient file in the patient database.

* * * * *